United States Patent [19]

Dettmar

[11] Patent Number: 4,652,446
[45] Date of Patent: Mar. 24, 1987

[54] PHARMACEUTICAL COMPOSITIONS
[75] Inventor: Peter W. Dettmar, Welwick, England
[73] Assignee: Reckitt & Colman Products Limited, Great Britain
[21] Appl. No.: 636,229
[22] Filed: Jul. 31, 1984
[30] Foreign Application Priority Data
  Sep. 2, 1983 [GB] United Kingdom ............... 8323624
[51] Int. Cl.$^4$ ...................... A61K 31/78; A61K 31/21
[52] U.S. Cl. ..................................... 424/81; 514/510
[58] Field of Search ........................... 424/81; 514/510
[56] References Cited
  U.S. PATENT DOCUMENTS
  2,912,358  11/1959  Staib ....................................... 424/81
  3,957,973   5/1976  Yamaguchi et al. .................. 424/81

OTHER PUBLICATIONS

Martindale, The Extra Pharmacopoeia, 28th ed., p. 77.

Primary Examiner—Frederick E. Waddell
Attorney, Agent, or Firm—Bacon & Thomas

[57] ABSTRACT

Pharmaceutical compositions comprising mixtures of sodium polyacrylate and carbenoxolone sodium in a specified range of ratios have been found to exhibit synergistic effects in an in vivo test model for anti-ulcer or mucosal-protecting agents. Pharmaceutical compositions comprising mixtures of sodium polyacrylate and carbenoxolone in the range of ratios are described for use in the treatment of gastritis or of gastro-duodenal ulcers.

11 Claims, No Drawings

PHARMACEUTICAL COMPOSITIONS

This invention relates to pharmaceutical compositions and in particular to compositions for the treatment of gastritis and gastro-duodenal ulcers.

Martindale, The Extra Pharmacopoeia 28th Ed, page 77 (1982) describes carbenoxolone sodium (the disodium salt of glycyrrhetinic acid hemisuccinate) and provides details of various preparations which have been developed for the treatment of gastric ulcers whether of the stomach, duodenum or oesophagus. Unfortunately, treatment with carbenoxolone sodium may be accompanied by side effects of varying severity such as fluid retention, congestive heart failure, hypertension and hypokalaemia and with the development of the powerful histamine $H_2$-receptor antagonists treatment has tended towards the use of drugs such as cimetidine and ranitidine.

Sodium polyacrylate has been suggested for use in the treatment of peptic ulcers. British Pat. No. 1435630 describes a solid antipeptic ulcer composition comprising sodium polyacrylate having an intrinsic viscosity of 0.3 or more and a pharmaceutically inert solid carrier. British Pat. No. 1538352 describes an improved composition which comprises granules of polyacrylic alkali metal salt coated with a water-insoluble but water permeable coating agent. Suitable polyacrylic alkali metal salts are stated to include sodium polyacrylate of molecular weight 3,000,000 to 8,000,000. The only specific sodium polyacrylate mentioned is one of molecular weight about 3,400,000.

We have carried out investigations into the mucosal-protective properties of carbenoxolone sodium and various acid polymers of natural and synthetic origin. We have surprisingly discovered that there is a synergistic effect when carbenoxolone sodium and sodium polyacrylate are mixed in certain proportions.

According to this invention there is provided a pharmaceutical composition comprising carbenoxolone sodium and sodium polyacrylate in a weight ratio of from 1:20 to 1:1, conveniently from 1:5 to 1:1 and preferably in a ratio of from 1:5 to 1:2.

As used herein "sodium polyacrylate" denotes the sodium salt of a polyacrylic acid which may be linear or cross-linked. Examples of commercial grades of linear polyacrylates are Carbopol 907 (free acid form B. F. Goodrich) and Aronvis (sodium salt Nihon Junyaku). Examples of commercial grades of cross-linked sodium polyacrylates are Rheogic 252L, Rheogic 250 H (Nihon Junyaku), and Hostacerin PN73 (Hoescht U.K. Ltd.) A preferred cross-linked polyacrylate is one of the carbomer range (free acid form).

In a preferred aspect of the invention there is provided a pharmaceutical composition comprising carbenoxolone sodium and carbomer sodium in a weight ratio of from 1:20 to 1:1, conveniently from 1:5 to 1:1 and preferably in a ratio of from 1:5 to 1:2.

Carbomer is described in the British Pharmacopeia and the United States National Formulary as being a synthetic high molecular weight cross-linked polymer of acrylic acid containing 56 to 68% of carboxylic acid groups. The British Pharmacopeia specifies cross-linking with allylsucrose. Carbomer is used in the form of neutralised gel as a suspending agent in pharmaceutical preparations for internal and external uses. U.S. Pat. No. 2,909,462 describes the use as a bulk laxative of a colloidally water-soluble polymer of acrylic acid cross-linked with from about 0.75% to 2.0% of polyallyl sucrose.

Examples of suitable commercial grades of carbomer are those sold by B. F. Goodrich under the Registered Trade Marks Carbopol 910, 934, 934P, 940 and 941. Other examples are those sold by Nihon Junyaku as Junlon PW110, Junlon PW150 and Junlon PW111, and Acrisint 400 (Sigma, Italy). In the compositions of the present invention the preferred material is carbomer 934P, having a molecular weight of approximately 3,000,000, a commercial grade being Carbopol 934P. (See USAN and the USP dictionary of drug names, USAN 1984 page 89).

The compositions of the invention are for oral administration and are preferably in the form of aqueous compositions having a pH of between 7.5 and 9.5. Where the polyacrylate used is in the acid form it is converted to the sodium form during the manufacturing process.

The invention also includes the use of carbenoxolone sodium and sodium polyacrylate in a weight ratio of from 1:20 to 1:1, conveniently from 1:5 to 1:1 and preferably in a ratio of 1:5 to 1:2 in the treatment of gastritis or gastro-duodenal ulcers.

In a further aspect the invention provides a method of treating gastritis or gastro-duodenal ulcers which comprises administering to a subject an orally effective amount of a pharmaceutical composition comprising carbenoxolone sodium and sodium polyacrylate in a weight ratio of from 1:20 to 1:1 and conveniently from 1:5 to 1:1.

In the treatment of gastritis or gastro-duodenal ulcers the normal dosage of carbenoxolone sodium will be in the range 40 to 5 mg and that of sodium polyacrylate in the range 200 to 5 mg provided that the weight ratio of carbenoxolone sodium to sodium polyacrylate falls within the range of 1:20 to 1:1 and conveniently in the range 1:5 to 1:1.

Because of the synergistic effect between the carbenoxolone sodium and sodium polyacrylate the present compositions afford the possibility of lower doses of carbenoxolone sodium being used with a resultant reduction in side effects.

The compositions may also include an antacid. Suitable materials include sodium bicarbonate, calcium carbonate, aluminium hydroxide and mixtures thereof. Use of these materials, in particular sodium bicarbonate, also results in a reduction in the viscosity of the liquid compositions, thereby providing some degree of viscosity control in the design of readily pourable liquid preparations.

For the treatment of inflamed or ulcerated portions of the oesophagus the compositions preferably also include sodium alginate together with amounts of calcium carbonate and sodium bicarbonate. In our British Pat. No. 1524740 we describe and claim a pharmaceutical composition comprising a low viscosity grade sodium alginate (as defined), from 0.16 to 2.60 parts by weight of sodium bicarbonate per weight of sodium alginate and from 0.10 to 1.04 parts by weight of calcium carbonate per weight of sodium alginate. When the compositions described in the patent contact the gastric acid a relatively rigid gelatinous precipitate of alginic acid is formed. The sodium bicarbonate and calcium carbonate present in the composition react with the gastric acid to form carbon dioxide which is entrapped in the gel. The carbonated gel having a lower bulk density then the gastric acid floats to the surface, the calcium ions serving to cross-link the precipitated alginic acid molecules and to strengthen the gel matrix. When gastric reflux takes place the low density carbonated gel passes into the lower portion of the oesophagus and contacts any inflamed or ulcerated portions thereof. When the synergistic combination of carbenoxolone sodium and sodium polyacrylate of the present invention is incorporated into the compositions of British Pat. No. 1524740 then the refluxed carbonated gel delivers the synergistic mixture to the inflamed or ulcerated portion of the oesophagus.

With aqueous compositions, which are susceptible to contamination and subsequent deterioration by microorganisms it is preferable to include a preservative. A suitable system is a combination of methyl and propyl-p-hydroxy benzoates or their sodium salts.

The pharmaceutical compositions of the present invention may also include one or more of a colouring, sweetening or flavouring agent.

The invention is illustrated by the following Examples.

EXAMPLE 1

A liquid preparation was prepared having the following formulation:

| | |
|---|---|
| carbenoxolone sodium | 0.20 g |
| Carbopol 934P | 0.42 g |
| sodium bicarbonate | 2.67 g |
| methyl p-hydroxybenzoate | 0.40 g |
| propyl p-hydroxybenzoate | 0.06 g |
| sodium hydroxide | 0.18 g |
| colour, flavouring, sweetener | 0.10 g |
| water to | 100.00 ml |

The Carbopol was dispersed with agitation in about 40 ml of water and then aqueous sodium hydroxide was added to give a gel. In a separate vessel carbenoxolone sodium, sodium bicarbonate, methyl and propyl p-hydroxybenzoates were added with agitation to about 50 mls of water. The Carbopol gel was then added to the mixture and thoroughly blended. Colour, flavouring and sweetener were then added followed by additional water to make up to a volume of 100 ml. The preparation had pH=7.8.

EXAMPLE 2

The formulation of the preparation of Example 1 was varied by the addition of 1.60 g calcium carbonate and 6.00 g sodium alginate (Protanal (Registered Trademark) LF 5/60, Protan & Fagertun, Norway). The preparation was prepared by a similar procedure to that of Example 1 with the two additional ingredients being blended in with the carbenoxolone sodium, sodium bicarbonate, methyl and propyl p-hydroxybenzoates.

EXAMPLES 3 TO 9

Set out below are details of further formulations prepared by the method described above for Example 1. Each Example contained 0.20 g carbenoxolone sodium, 0.149 g methyl p-hydroxybenzoate sodium, 0.022 g propyl p-hydroxybenzoate sodium and water to 100 ml.

| Example No. | 3 | 4 | 5 | 6 | 7 | 8 | 9 | |
|---|---|---|---|---|---|---|---|---|
| Carbopol 934P | 0.42 | 0.42 | 0.42 | 1.00 | 0.42 | 1.0 | 1.0 | g |
| sodium bicarbonate | — | 2.67 | — | 2.67 | 1.34 | 1.34 | 2.67 | g |
| calcium carbonate | — | — | 2.24 | — | 1.12 | 1.12 | 2.24 | g |
| sodium hydroxide | 0.18 | 0.18 | 0.18 | 0.43 | 0.18 | 0.43 | 0.43 | g |
| pH | 7.7 | 7.8 | 8.8 | 7.8 | 8.1 | 7.8 | 7.8 | |

EXAMPLES 10 TO 15

The following further examples were prepared by the method as described in Example 1. Each example contained 1.0 g Carbopol 934P, 0.43 g sodium hydroxide, 0.149 g methyl p-hydroxybenzoate sodium, 0.022 g propyl p-hydroxybenzoate sodium, 0.1 g colour, flavouring and sweetener, and water to 100 ml.

| Example No. | 10 | 11 | 12 | 13 | 14 | 15 | |
|---|---|---|---|---|---|---|---|
| Carbenoxolone sodium | 0.1 | 0.2 | 0.1 | 0.2 | 0.075 | 0.05 | g |
| sodium bicarbonate | 1.0 | 1.0 | 1.0 | 1.0 | 1.0 | 1.0 | g |
| calcium carbonate | 1.0 | 1.0 | — | — | 1.0 | 1.0 | g |
| aluminium oxide (as aluminium hydroxide gel) | — | — | 1.0 | 1.0 | — | — | g |
| pH | 8.5 | 8.5 | 8.3 | 8.2 | 8.4 | 8.6 | |

EXAMPLE 16

A liquid preparation was prepared by the method as described in Example 1 having the composition:

| | |
|---|---|
| carbenoxolone sodium | 0.20 g |
| Carbopol 910 | 2.00 g |
| sodium bicarbonate | 1.00 g |
| methyl p-hydroxybenzoate sodium | 0.149 g |
| propyl p-hydroxybenzoate sodium | 0.022 g |
| sodium hydroxide | 0.86 g |
| colour, flavouring, sweetener | 0.10 g |
| water to | 100.00 ml |
| pH = 8.3 | |

EXAMPLE 17

Carbopol 934P sodium salt was prepared by dispersing 1 kg Carbopol 934P in a solution of 400 g sodium hydroxide in 3.6 kg anhydrous methanol. The salt was collected by filtration, dried and comminuted.

750 g Carbopol 934P sodium salt was blended with 150 g carbenoxolone sodium and 1350 g powdered lactose. The powder blend was mixed, in a planetary mixer with 1.5 L of a 10% w/v solution of polyvinyl pyrrolidone (povidone K30) in isopropanol, and the wet mass passed through an oscillating granulator fitted with a 750 μm screen. The granules were dried and screened through a 750 μm sieve.

320 mg Units of these granules, each containing 100 mg Carbopol 934P sodium salt and 20 mg carbenoxolone sodium were filled into size 1 hard gelatine capsules.

EXAMPLE 18

250 g Carbopol 934P sodium salt was blended with 50 g carbenoxolone sodium and 2.5 Kg lactose. The powder was mixed, in a planetary mixer with 1.75 L of a 20% w/v solution of polyvinyl pyrrolidone (povidone K30) in isopropanol, and the wet mass forced through a 750 μm screen in an oscillating granulator. The granules were dried and rescreened through a 750 μm sieve.

1.26 g Units of these granules, each containing 100 mg Carbopol 934P sodium salt and 20 mg carbenoxolone sodium, were filled into laminate sachets. [The contents of the sachet are mixed with water (preferably 20–100 ml) prior to administration].

The pharmaceutical properties of the compositions of the invention have been evaluated in two in vivo rat models.

The anti-ulcer or mucosal-protecting properties were determined in the ethanol-induced gastric necrosis test by a method based on that of Robert A., Nezamis J. E., Lancaster C. and Hanchar A. J., Gastroenterology 77, 433, (1979).

In the test method male Sprague-Dawley rats (150–170 g) were housed singly and fasted for 18 hours and deprived of water for 4 hours prior to the treatment. Drug or drug vehicle was administered orally (n=10 per group) in a dose volume of 5 ml/kg. Thirty minutes later the rats were dosed orally with 80% ethanol (in a dose volume of 5 ml/kg). One hour later the rats were killed by cervical dislocation. The abdomen was opened immediately and the stomach exposed. The stomach was tied off at the base of the oesophagus and then removed with 4 to 5 cms of duodenum attached. The gastric contents were flushed out twice with water, then the stomach was inflated using 70% (Industrial Methylated Spirits) and stored in 70% IMS prior to examination. The stomach was opened along the greater curvature and the mucosa was examined by an observer who was unaware of the treatment given. The lesions were measured in millimeters in a systematic manner, their length recorded, and the total lesion length per stomach was determined. The code was broken after all the stomachs had been examined and the severity of the lesion damage was expressed as the mean total lesion length (±SEM) per group of rats. Statistical analysis of the date was performed using student's 't' test for unpaired data. A pretreatment effect was considered significant if the p value was less than 0.05. The control vehicle treated group mean was compared to that of the drug treated group and the percentage protection from the lesion damage caused by ethanol was determined.

Table 1 presents test data obtained with compositions having pH 8.0 containing either carbenoxolone (sodium salt) or Carbopol 934P (sodium salt) and Table 2 presents data for compositions of pH 8.0 containing varying amounts of the two components.

TABLE 1

| Treatment | Dose % | % Protection | p Values |
| --- | --- | --- | --- |
| Carbenoxolone | 0.2 | 0 | NS |
|  | 0.6 | 26.4 | NS |
|  | 1.2 | 69.1 | <0.01 |
|  | 2.0 | 93.6 | <0.001 |
|  | 6.0 | 100 | <0.001 |
| Carbopol 934P | 0.42 | 2.9 | NS |
|  | 0.5 | 25.8 | NS |
|  | 1.0 | 39.1 | <0.02 |
|  | 2.0 | 34.5 | <0.05 |

TABLE 2

| Treatment (Dose %) Carbopol 934P + Carbenoxolone | | % Protection | p Values |
| --- | --- | --- | --- |
| 0.42 | — | 2.9 | NS |
| — | 0.2 | 0 | NS |
| 0.11 | 0.2 | 0 | NS |
| 0.21 | 0.2 | 25.3 | NS |
| 0.42 | 0.05 | 30.1 | NS |
| 0.42 | 0.1 | 32.9 | NS |
| 0.42 | 0.2 | 66.6 | <0.001 |

From Table 1 it can be seen that the minimum doses to significantly protect against the ethanol-induced gastric necrosis were 1.2% of carbenoxolone (69.1% protection, p<0.01) and 1% of Carbopol 934P (39.1% protection, p<0.02). Unlike carbenoxolone the Carbopol did not achieve greater than 40% protection against the effect of the ethanol.

From Table 2 it can be seen that when an inactive dose of Carbopol 934P (0.42%) was combined with an inactive dose of carbenoxolone (0.2%) significant protection (66.6%, p<0.001) was produced, i.e. synergism is exhibited.

The ability of the compositions to bind (adhere) to the rat gastric mucosa was determined by a method based on that of Green A. P., Lander J. E. and Turner D. H., J. Pharm. Pharmacol. 33, 348, (1981). The method employs a cationic dye, alcian blue, that binds to acidic mucopolysaccharides present in gastric mucus. In vitro, this dye gives a positive reaction with polysaccharides e.g. k-carrageanan, aliginate, carboxymethyl cellulose and xanthan, and polyacrylates e.g. carbomer.

In the test method male Sprague-Dawley rats (130–150 g) were housed singly and fasted overnight for 18 hours before treatment. Following treatment (administered orally in a dose volume of 5 ml/kg) the rats (n=10 per group) were left for a further 60 minutes before being killed by cervical dislocation. The abdomen was opened immediately, the stomach was dissected out, freed of any connective tissue and opened along the greater curvature. The stomachs were gently washed under lightly running water and placed into 10 ml of ice-cold 0.25M sucrose solution. The stomachs in the sucrose sollution were then weighed on an electronic balance (Sartorius 1212 MP) and the approximate wet weight of each stomach was determined. The stomachs were removed from the sucrose solution and lightly shaken with forceps to remove excess sucrose. The washed stomachs were then incubated in 10 ml of freshly prepared Alcian Blue 8GX (Aldrich Chemical) dye solution (1 mg/ml), in 0.15M sucrose buffered with 0.05M sodium acetate that had been adjusted to pH 5.8 with HCl, for two hours at room temperature with an occasional shake. The stomachs (now blue) were washed for 10 minutes with 10 ml 0.25M sucrose solution (2x), lightly shaken with forceps to remove excess sucrose and placed in 15 ml of 0.5M magnesium chloride solution for a further two hours at room temperature, shaken occasionally, and removed. The blue magnesium chloride solution was shaken for ~30 seconds with ~3 ml diethyl ether (2x). The optical density of the aqueous layer was measured using disposable cuvettes (4 ml capacity, 1 cm light path) on a Cecil 595 dual beam spectrophotometer at 605 nm. The blank used to compare all the samples (Reference cuvette) was magnesium chloride solution. The results are expressed in optical density units per g tissue weight. Statistical analysis of the data was performed using student's 't' test for unpaired data. A pretreatment effect was considered significant if the p value was less than 0.05. The percentage difference between the control and test groups was also determined.

Table 3 presents test data obtained with compositions having pH 8.0 containing Carbopol 934P (sodium salt) at various concentrations determined 60 minutes after dosing and Table 4 presents the results for compositions having pH 8.0 containing 1% Carbopol 934P (sodium salt) determined at times over 6 hours.

TABLE 3

| % Carbopol 934P | % Increase in binding | p Value |
|---|---|---|
| 0.1 | 11.5 | NS |
| 0.2 | 18.8 | <0.05 |
| 0.5 | 75.2 | <0.001 |
| 1.0 | 118.9 | <0.001 |

TABLE 4

| Time post dose (h) | % Increase in binding | p Value |
|---|---|---|
| 0.5 | 109.5 | <0.001 |
| 1 | 118.9 | <0.001 |
| 2 | 58.1 | <0.001 |
| 3 | 65.0 | <0.001 |
| 4 | 36.2 | <0.01 |
| 5 | 36.3 | <0.01 |
| 6 | 6.0 | NS |

From Table 3 it can be seen that Carbopol 934P (sodium salt) readily binds to the rat gastric mucosa in a dose related manner. From Table 4 it can be seen that the binding persisted for up to five hours.

Further investigations were carried out using the two in vivo rat models with the Carbopol 934P being replaced by other acidic polymers. Table 5 presents test data for the compositions having pH 8.0 of the acidic polymers (sodium salt) alone in the two tests. Table 6 presents data on combinations with carbenoxolone (sodium salt 0.2%) in the ethanol induced necrosis test.

TABLE 5

| Polymer (dosed po, 1%) | Ionic function | % Protection rat ethanol test | P Value | % increase in Binding to rat gastric mucosa | P Value |
|---|---|---|---|---|---|
| Carbopol 934P | $CO_2-$ | 39.1 | <0.02 | 118.9 | <0.001 |
| Carboxymethyl cellulose | $CO_2-$ | 39.2 | <0.05 | 0 | NS |
| Alginate* | $CO_2-$ | 21.8 | NS | 8.3 | NS |
| k-Carrageenan | $SO_4-$ | 36.1 | <0.05 | 0 | NS |
| Xanthan gum | $CO_2-$ | 17.0 | NS | 5 | NS |

*Dosed (po) at 6%

TABLE 6

| | | % Protection | | | |
|---|---|---|---|---|---|
| Polymer (dosed po) | Dose % | Alone | P Value | +Carbenoxolone (0.2%) | P Value |
| Carbopol 934P | 0.42 | 2.9 | NS | 66.6 | <0.001 |
| Carboxymethyl cellulose | 1.0 | 39.2 | <0.05 | 0 | NS |
| k-Carrageenan | 1.0 | 36.1 | <0.05 | 34.4 | NS |
| Alginate | 2.0 | 32.0 | NS | 12.7 | NS |

From Table 5 it can be seen that whilst sodium carboxymethyl cellulose and k-carrageenan (a sulphated polysaccharide) both produced a degree of protection in the rat ethanol necrosis test similar to that found with Carbopol 934P neither polymer demonstrated any significant binding affinity for the rat gastric mucosa in vivo. Sodium alginate and xanthan gum failed to produce significant results in either test. Table 6 shows that of the polymers tested only Carbopol 934P demonstrated synergism when combined with carbenoxolone in the rat ethanol necrosis test.

Table 7 presents test data obtained in binding studies with compositions containing 0.5% of the sodium salts of various polyacrylates as determined 60 minutes after dosing.

TABLE 7

| Polyacrylate | pH | % Increase in binding | p Value |
|---|---|---|---|
| Crosslinked | | | |
| Carbopol 934P | 8.0 | 75.2 | <0.001 |
| Carbopol 940 | 8.2 | 92.6 | <0.001 |
| Carbopol 941 | 8.4 | 79.7 | <0.001 |
| Rheogic 250H | 7.8 | 33.3 | <0.001 |
| Junlon PW110 | 8.0 | 54.2 | <0.001 |
| Acrisint 400 | 8.8 | 102.7 | <0.001 |
| Rheogic 252L | 7.9 | 44.7 | <0.001 |
| Junlon PW150 | 8.5 | 63.5 | <0.001 |
| Carbopol 910 | 9.4 | 44.3 | <0.001 |
| Linear | | | |
| Aronvis | 8.2 | 41.2 | <0.001 |
| Carbopol 907 | 8.5 | 37.6 | <0.001 |

From Table 7 it can be seen that with the sodium salts of all the polyacrylates tested there was an increase in binding.

Table 8 presents test data obtained with Examples in the rat ethanol necrosis test.

TABLE 8

| Treatment | % Protection | p Value |
|---|---|---|
| Example 1 | 76.1 | <0.001 |
| Example 2 | 88.8 | <0.01 |
| Example 3 | 57.9 | <0.01 |
| Example 10 | 92.5 | <0.001 |
| Example 11 | 94.0 | <0.001 |
| Example 12 | 68.4 | <0.01 |
| Example 13 | 71.8 | <0.01 |
| Example 14 | 87.8 | <0.001 |
| Example 15 | 72.2 | <0.001 |

We claim:

1. A pharmaceutical composition for oral administration comprising from 5 to 40 mg carbenoxolone sodium and from 5 to 200 mg sodium polyacrylate in a weight ratio of 1:20 to 1:1.

2. A pharmaceutical composition according to claim 1 comprising carbenoxolone sodium and sodium polyacrylate in a weight ratio of 1:5 to 1:1.

3. A pharmaceutical composition according to claim 1 wherein the ratio is between 1:5 and 1:2.

4. A pharmaceutical composition according to claim 1 wherein the sodium polyacrylate is carbomer sodium.

5. A pharmaceutical composition according to claim 4 wherein the carbomer has a molecular weight of about 3,000,000.

6. A pharmaceutical composition according to claim 1 which further includes an antacid.

7. A pharmaceutical composition according to claim 6 wherein the antacid is sodium bicarbonate, calcium carbonate or aluminium hydroxide, or mixtures thereof.

8. A pharmaceutical composition according to claim 1 which further includes sodium alginate together with calcium carbonate and sodium bicarbonate.

9. A pharmaceutical composition according to claim 1 in the form of an aqueous composition having a pH of between 7.5 and 9.5.

10. A method of treating ethanol-induced gastritis or gastro-duodenal ulcers which comprises administering to a patient an orally effective amount of a pharmaceutical composition comprising from 5 to 40 mg carbenoxolone sodium and from 5 to 200 mg sodium polyacrylate in a weight ratio of 1:20 to 1:1.

11. A method of treating ethanol-induced gastritis or gastro-duodenal ulcers which comprises adinistering to a patient an orally effective amount of a pharmaceutical composition comprising from 5 to 40 mg carbenoxolone sodium and from 5 to 200 mg sodium polyacrylate in a weight ratio of 1:5 to 1:1.

* * * * *